US006132963A

United States Patent [19]
Brent et al.

[11] Patent Number: 6,132,963
[45] Date of Patent: *Oct. 17, 2000

[54] INTERACTION TRAP SYSTEMS FOR ANALYSIS OF PROTEIN NETWORKS

[75] Inventors: Roger Brent, Cambridge; Russell L. Finley, Jr., Belmont, both of Mass.

[73] Assignee: The General Hosptial Corporation, Boston, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/949,376

[22] Filed: Oct. 14, 1997

Related U.S. Application Data

[63] Continuation of application No. 08/783,534, Jan. 14, 1997, Pat. No. 5,695,941, which is a continuation of application No. 08/263,566, Jun. 22, 1994, abandoned.

[51] Int. Cl.$^7$ .............................. C12Q 1/68; G01N 33/53
[52] U.S. Cl. ................................................ 435/6; 435/7.1
[58] Field of Search ....................... 536/23.4; 435/320.1, 435/172.3, 325, 254.2, 254.21, 6, 7.1

[56] References Cited

U.S. PATENT DOCUMENTS

| | | | |
|---|---|---|---|
| 5,283,173 | 2/1994 | Fields et al. .................................. | 435/6 |
| 5,580,736 | 12/1996 | Brent et al. .................................. | 435/6 |

OTHER PUBLICATIONS

Alani et al., "A method for gene disruption that allows repeated use of URA 3 selection in the construction of mulitply disrupted yeast strains," Genetics 116:541–545 (1987).

Bartel et al., "Using the two hybrid system to detect protein–protein interactions" in *Cellular Interactions in Development*, ed. Hartley, New York: IRL Press pp. 153–179 (1994).

Bendixen et al., "A Yeast Mating–Selection Scheme for Detection of Protein–Protein Interactions," Nucleic Acids Research 22:1778–1779 (1994).

Brent et al., Nature 312:612–615 (1984).

Brent et al., "A Eukaryotic Transcriptional Activator Bearing the DNA Specificity of a Prokaryotic Repressor," Cell 43:729–736 (1985).

Broach et al., "Transformation in yeast: Development of a hybrid cloning vector and isolation of the can–1 gene," Gene 8: 121–133 (1979).

Celenza et al., "A Yeast Gene That is Essential for Release from glucose Repression Encodes a Protein Repression Encodes a Protein Kinase," Science 233:1175–1180 (1986).

Celenza et al., "Molecular Analysis of the SNF4 Gene of *Saccharomyces cerevisiae:* Evidence for Physical Association ofthe SNF4 Protein with SNF1 Protein Kinase," Molecular and Cellular Biology 9:5045–5054 (1989).

Celenza et al., "Mutational Analysis of the *Saccharomyces cerevisiae* SNF1 Protein Kinase and Evidence for Functional Interaction withthe SNF4 Protein Kinase and Evidence for Functional Interaction with the SNF4 Protein," Molecular and Cellular Biology 9:5034–5044 (1989).

Chien et al., "The two–hybrid system: A method to identify and clone genes for proteins that interact with a protein of interest," Proc. Natl. Acad. Sci. USA 88:9578–9582 (1991).

Curran et al., "Fos and Jun: The ap–1 Connection," Cell 55:395–397 (1988).

Dalton et al., "Characterization of SAP–1, a Protein Recruited by Serum Response Factor to the c–fos Serum Response Element," Cell 68:597–612 (1992).

Dang et al., "Intracellular Leucine Zipper Interactions Suggest c–Myc Hetero–Oligomerization," Cellular Biology 11:954–962 (1991).

Davidson and Sauer, Proc. Natl. Acad. Sci. USA 91:2146–2150 (1994).

Draetta, Trends in Biochem. Sci. 15:378–382 (1990).

Fearon et al., "Karyoplasmic interaction selection strategy: A general strategy to detect protein–protein interactions in mammalian cells," Proc. Natl. Acad. Sci. USA 89:7958–7962 (1992).

Fields and Song, Nature 340:245–246 (1989).

Fields et al., "The two–hybrid system: an assay for protein–protein interactions," Trends in Genetics 10:286–292 (1994).

Furey et al., "Crystal Structure of Cd, Zn Metallothionein," Science 231:704–707 (1986).

Gill et al., Nature 334:721–724 (1988).

Gill et al., "Mutants of GAL4 Protein Altered in an Activation Function," Cell 51:121–126.

Goff et al., "Functional analysis of the transcriptional activator encoded by the maize B gene: evidence for a direct functional interaction . . . ," Genes & Development 5:864–875 (1992).

Hadwiger et al., Proc. Natl. Acad. Sci. USA 86:6255–6259 (1989).

Hardy et al., "A RAP1–interacting protein involved in transcriptional silencing and telomere length regulation," Genes & Development 6:801–814 (1992).

Harper et al., "The p21 Cdk–interacting protein Cipl is a potent inhibitor of G1 cyclin–dependent kinases," Cell 75:805–816 (1993).

Hope et al., "Functional Dissection of a Eukaryotic Transcriptional Activator Protein, GCN4 of Yeast," Cell 46:885–894 (1986).

Hope et al., "Structural and Functional Characterization of the Short Acidic Transcriptional Activation Region of Yeast GCN4 Protein," Nature 333:635–640 (1988).

Hu et al., "Sequence Requirements for Coned–Coils: Analysis with Repressor–GCN4 Leucine Zipper Fusions," Science 250:1400–1403 (1990).

(List continued on next page.)

*Primary Examiner*—Robert A. Schwartzman
*Attorney, Agent, or Firm*—Clark & Elbing LLP

[57] ABSTRACT

Disclosed are sets of DNA molecules, and cell containing such molecules, each molecule encoding a candidate interacting protein fused to either a DNA binding domain or a gene activating domain to which it is not naturally bonded.

5 Claims, 1 Drawing Sheet

OTHER PUBLICATIONS

Johnston, "A Model Fungal Gene Regulatory Mechanism: the GAL Genes of *Saccharomyces Cerevisiae*," Microbiological Review 51:458–476 (1987).

Keegan et al., "Separation of DNA Binding from the Transcription–Activating Function of Eukaryotic Regulatory Protein," Science 231:699–704 (1986).

Koff et al., Cell 66:1217–1228 (1991).

Kumar et al., "Functional Domains of the Human Estrogen Receptor," Cell 51:941–951 (1987).

Laughon et al., "Primary Structure of the *Saccharomyces cerevisiae* GAL4 Gene," Cellular Biology 4:260–267 (1984).

Lee et al., Protein Engineering 6:745–754 (1993).

Ma et al., "A New Class of Yeast Transcriptional Activators," Cell 51:113–119 (1987).

Ma et al., "Converting a Eukaryotic Transcriptional Inhibitor into an Activator," Cell 55:443–446 (1988).

Ma et al., "Deletion Analysis of GAL4 Defines Tow Transcriptional Activating Segments," Cell 48:847–853 (1987).

Martin et al., "Genetic Exploration of Interactive Domains in RNA Polymerase II Subunits," Cellular Biology 10:1908–1914 (1990).

McKnight et al., "Binding of the Virion Protein Mediating Gene Induction in Herpes Simplex Virus 1–Infected Cells to its cis Site Requires Cellular Proteins," Proc. Natl. Acad. Sci. USA 84:7061–7065 (1987).

Meyerson et al., The EMBO Journal 11:2909–2917 (1992).

Pines et al., Cell 59:833–846 (1989).

Richardson et al., Cell 59:1127–1133 (1989).

Richardson et al., Genes & Development 4:1332–1344 (1990).

Silver et al., "Amino Terminus of the Yeast GAL4 Gene Product is Sufficient for Nuclear Localization," Proc. Natl. Acad. Sci. USA 81:5951–5955 (1984).

Thukral et al., "Localization of a Minimal Binding Domain and Activation Regions in Yeast Regulatory Protein ADR1," American Society for Microbiology 9:2360–2369 (1989).

Touchette, The Journal of NIH Research 3:44–46 (1991).

Tsai et al., Nature 353:174–177 (1991).

Wittekind et al., "Isolation and Characterization of Temperature–Sensitive Mutations in RPA190, the Gene Encoding the Largest Subunit of RNA Polymerase . . . ," Cellular Biology 8:3997–4008 (1988).

Wittenberg et al., Molecular and Cellular Biology 9:4064–4068 (1989).

Wittenberg et al., Cell 54:1061–1072 (1988).

Wittenberg et al., Cell 62:225–237 (1990).

Xiong et al., Cell 65:691–699 (1991).

Yang et al., Science 257:680–682 (1992).

Zervos et al., "Mxil, a protein that specifically interacts with Max to bind myc–max recognition sites," Cell 72:223–232 (1993).

Li et al., "Identification of mutations in p53 that affect its binding to SV40 large T antigin by using the yeast tw–hybrid system", FASEB J. 7:957–963, Jul. 1993.

Vojtek et al., "Mammalian ras interacts directly with the serine/threonine kinase raf", Cell 74: 205–214, Jul. 1993.

Mitcham et al., "Use of the two–hybrid system to isolate components of the interleukin–1 signalling pathway", J. Cell. Biochem. 18B: 284, Feb. 1994.

1

INTERACTION TRAP SYSTEMS FOR ANALYSIS OF PROTEIN NETWORKS

This is a continuation of application Ser. No. 08/783,534, filed Jan. 14, 1997, U.S. Pat. No. 5,695,941, which is a continuation of application Ser. No. 08/263,566, filed Jun. 22, 1994, now abandoned.

BACKGROUND OF THE INVENTION

This invention relates to in vivo methods for detecting protein interactions and isolating novel proteins.

Many cell cycle regulatory proteins have been identified using yeast two-hybrid systems like the interaction trap (Gyuris et al., Cell 75:791, 1993; Harper et al., Cell 75:805, 1993; Serrano et al., Nature 366:704, 1993; Hannon et al., Genes & Dev. 7:2378, 1993). In two-hybrid systems (Fields and Song, Nature 340:245, 1989), two proteins are expressed in yeast: one contains a DNA-binding moiety (the "bait", the other a transcription activation domain. If the proteins interact, they activate transcription of a reporter gene that contains a binding site for the DNA-binding protein. Typically, the interaction trap (Gyuris et al., supra) uses E. coli LexA repressor as the DNA-binding moiety and two different reporter genes, LEU2 and lacz, that each contain upstream LexA operators. Proteins that may interact with the bait, such as those encoded by members of cDNA libraries, are fused to an activation domain and expressed conditionally under the control of the yeast GAL1 promoter. To conduct an interactor hunt, cells that contain a bait are transformed with a library plasmid that expresses activation-tagged cDNA proteins, and transformants that contain proteins that associate with the bait are selected because they grow in the absence of leucine and form blue colonies on X-Gal medium. The most sensitive LEU2 reporter allows detection of interacting proteins with estimated $K_d$s less than $10^{-6}$M (Gyuris et al., supra). Interacting proteins specific for the bait are identified as those that do not interact with unrelated baits.

SUMMARY OF THE INVENTION

In general, in one aspect, the invention involves a method for determining whether at least three proteins are capable of interacting with each other. This method involves: (a) providing a first host cell which contains (i) a reporter gene operably linked to a protein binding site; (ii) a first fusion gene which expresses a first fusion protein, the first fusion protein including a first protein covalently bonded to a binding moiety which is capable of specifically binding to the protein binding site; and (iii) a second fusion gene which expresses a second fusion protein, the second fusion protein including a second protein covalently bonded to a gene activating moiety; (b) measuring reporter gene expression in the first host cell, an increase in expression indicating an interaction between the first and second proteins; (c) providing a second host cell which contains (i) the reporter gene; (ii) the first fusion gene; and (iii) a third fusion gene which expresses a third fusion protein, the third fusion protein including a third protein covalently bonded to a gene activating moiety; (d) measuring reporter gene expression in the second host cell, an increase in expression indicating an interaction between the first and third proteins; (e) constructing a fourth fusion gene which expresses a fourth fusion protein, the fourth fusion protein including the protein binding site covalently bonded to a second protein shown in step (b) to be capable of interacting with the first protein; (f) introducing into a third host cell (i) the reporter gene; (ii) the third fusion gene; and (iii) the fourth fusion gene; and (g) measuring reporter gene expression in the third host cell, an increase in expression indicating an interaction between the second and third proteins.

In a second aspect, the invention involves a method for determining whether a first mammalian protein is capable of interacting with a second mammalian protein. This method involves: (a) providing a first yeast cell which contains (i) a reporter gene operably linked to a protein binding site; and (ii) a first fusion gene which expresses a first fusion protein, the first fusion protein including the first mammalian protein covalently bonded to a binding moiety which is capable of specifically binding to the protein binding site; (b) providing a second yeast cell which contains a second fusion gene which expresses a second fusion protein, the second fusion protein including the second mammalian protein covalently bonded to a gene activating moiety; (c) mating the first yeast cell with the second yeast cell; and (d) measuring reporter gene expression, an increase in expression indicating an interaction between the first and the second mammalian proteins.

In preferred embodiments of both of the above methods, the gene activating domain is a weak gene activating domain; the host cells contain a second reporter gene, the second reporter gene being different than the first reporter gene (for example, a LEU2 gene and a lacZ gene); the host cell is a yeast cell; the protein binding site is a LexA binding site and the binding moiety comprises a LexA DNA binding domain; the reporter gene is assayed by a color reaction; the reporter gene is assayed by cell viability.

In a third aspect, the invention features a set of DNA molecules, each molecule encoding a candidate interacting protein fused to a DNA binding domain to which it is not naturally bonded.

In a fourth aspect, the invention features a set of DNA molecules, each molecule encoding a candidate interacting protein fused to a weak gene activating domain to which it is not naturally bonded.

In preferred embodiments of both the third and fourth aspects, each of the candidate interacting proteins is involved in signal transduction; each of the candidate interacting proteins is a cytokine; each of the candidate interacting proteins is involved in DNA replication; each of the candidate interacting proteins is involved in a function occurring in the cell nucleus; and each of the candidate interacting proteins is involved in intermediary metabolism.

In a fifth aspect, the invention features a set of eukaryotic cells (preferably, yeast cells), each cell containing one of the set of DNA molecules of the third and fourth aspects.

In a sixth aspect, the invention features a pair of haploid yeast cells, the first cell of the pair containing (a) a reporter gene operably linked to a protein binding site; and (b) a first fusion gene which expresses a first fusion protein, the first fusion protein including a first protein covalently bonded to a binding moiety which is capable of specifically binding to the protein binding site; and the second cell of the pair containing a second fusion gene which expresses a second fusion protein, the second fusion protein including a second protein covalently bonded to a gene activating moiety. In preferred embodiments, the second cell further contains a second reporter gene, said second reporter gene being different than the first reporter gene.

As used herein, by "reporter gene" is meant a gene whose expression may be assayed; such genes include, without limitation, lacZ, amino acid biosynthetic genes, e.g. the yeast LEU2, HIS3, LYS2, TRP1, or URA3 genes, nucleic acid biosynthetic genes, the mammalian chloramphenicol transacetylase (CAT) gene or GUS gene, or any surface antigen gene for which specific antibodies are available. Reporter genes may encode any enzyme that provides a phenotypic marker, for example, a protein that is necessary for cell growth or a toxic protein leading to cell death, or one encoding a protein detectable by color assay or one whose expression leads to an absence of color. Particularly preferred reporter genes are those encoding fluorescent markers, such as the GFP gene (i.e., Green Fluorescent Protein gene). Reporter genes may facilitate either a selection or a screen for reporter gene expression, and quantitative differences in reporter gene expression may be measured as an indication of interaction affinities.

By "operably linked" is meant that a gene and a regulatory sequence(s) are connected in such a way as to permit gene expression when the appropriate molecules (e.g., transcriptional activator proteins or proteins which include transcriptional activation domains) are bound to the regulatory sequence(s).

By "covalently bonded" is meant that two domains are joined by covalent bonds, directly or indirectly. That is, the "covalently bonded" proteins or protein moieties may be immediately contiguous or may be separated by stretches of one or more amino acids within the same fusion protein.

By "protein" is meant a sequence of amino acids, constituting all or a part of a naturally-occurring polypeptide or peptide, or constituting a non-naturally-occurring polypeptide or peptide.

By a "binding moiety" is meant a stretch of amino acids which is capable of directing specific polypeptide binding to a particular DNA sequence (i.e., a "protein binding site").

By "weak gene activating moiety" is meant a stretch of amino acids which is capable of weakly inducing the expression of a gene to whose control region it is bound. As used herein, "weakly" is meant below the level of activation effected by GAL4 activation region II (Ma and Ptashne, Cell 48:847, 1987) and is preferably at or below the level of activation effected by the B112 activation domain of Ma and Ptashne (Cell 51:113, 1987). One preferred weak gene activating moiety is the B42 domain of Ma and Ptashne (supra). Levels of activation may be measured using any downstream reporter gene system and comparing, in parallel assays, the level of expression stimulated by the GAL4 region II-polypeptide with the level of expression stimulated by the polypeptide to be tested.

By "set" is meant 5 or more (as used herein) DNA molecules or eukaryotic cells. Preferably, such a set includes at least 10 different DNA molecules or eukaryotic cells, more preferably 25 different DNA molecules or eukaryotic cells, and most preferably 100's or even 1000's of different DNA molecules or eukaryotic cells.

The interaction trap systems described herein provide advantages over more conventional methods for isolating interacting proteins or genes encoding interacting proteins. For example, applicants' systems provide rapid and inexpensive methods having very general utility for identifying and purifying genes encoding a wide range of useful proteins based on the protein's physical interaction with a polypeptide of known diagnostic or therapeutic usefulness. This general utility derives in part from the fact that the components of the systems can be readily modified to facilitate detection of protein interactions of widely varying affinity (e.g., by using reporter genes which differ quantitatively in their sensitivity to a protein interaction). Inducible promoters used to express the interacting proteins further increase the scope of candidate interactors which may be detected since even proteins whose chronic expression is toxic to the host cell may be isolated simply by inducing a short burst of the protein's expression and testing for its ability to interact and stimulate expression of a reporter gene.

If desired, detection of interacting proteins may be accomplished through the use of weak gene activation domain tags. This approach avoids restrictions on the pool of available candidate interacting proteins which may be associated with stronger activation domains (such as GAL4 or VP16); although the mechanism is unclear, such a restriction apparently results from low to moderate levels of host cell toxicity mediated by the strong activation domain.

In addition, certain of the claimed methods facilitate the ready identification of higher order protein interactions, for example, protein interactions involving three or more polypeptides. Certain other claimed methods exploit a yeast mating assay to rapidly screen for interactions among extremely large numbers of mammalian proteins. According to this method, an uncharacterized protein is introduced by mating into an extensive panel of yeast strains, each carrying a different putative interacting protein, and interactions are identified, for example, through visual screening. Identification of protein interactions provides important knowledge regarding the protein's function and also provides immediate access to mammalian proteins of interest.

Other features and advantages of the invention will be apparent from the following detailed description thereof, and from the claims. These examples are designed to illustrate, not limit, the invention.

BRIEF DESCRIPTION OF THE DRAWING

The drawing is first briefly described.

DETAILED DESCRIPTION

Figure 1:
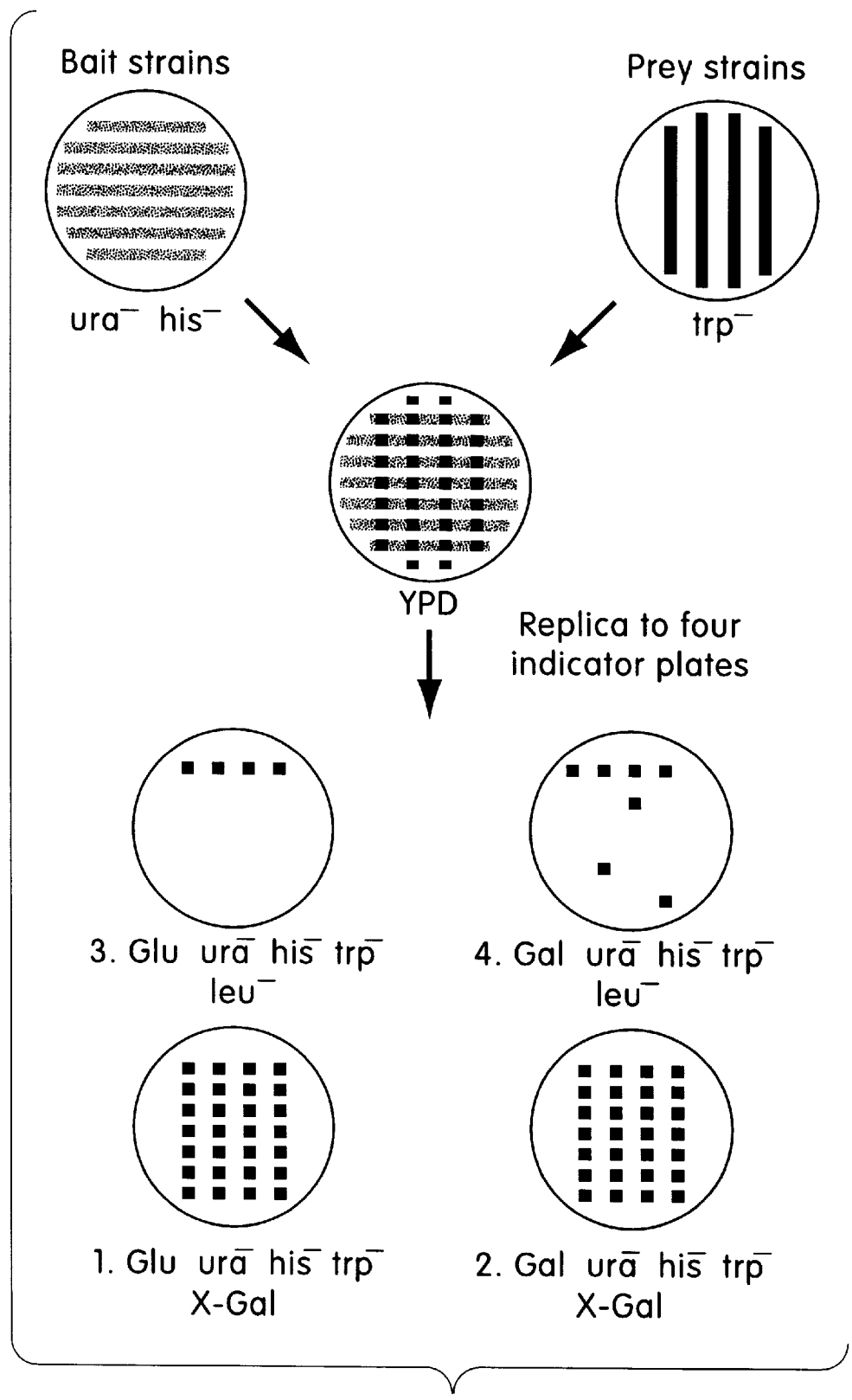
FIG. 1 is a schematic drawing of one embodiment of the interaction mating system.

Applicants have developed a variety of in vivo interaction trap systems for the isolation of genes encoding proteins which physically interact with other proteins of known diagnostic or therapeutic utility. In general, the systems involve eukaryotic host strains (e.g., yeast strains) which are engineered to express a protein of therapeutic or diagnostic interest as a fusion protein covalently bonded to a known DNA binding domain; this protein is referred to as a "bait" protein because its purpose in the system is to "catch" useful, but as yet unknown or uncharacterized, interacting polypeptides (termed the "prey"; see below). The eukaryotic host strain also contains one or more "reporter genes," i.e., genes whose transcription is detected in response to a bait-prey interaction. Bait proteins, via their DNA binding domain, bind to their specific DNA site upstream of a reporter gene; reporter transcription is not stimulated, however, because the bait protein lacks its own activation domain.

To isolate genes encoding novel interacting proteins, members of a DNA (e.g., a cDNA) expression library are introduced into the strain containing the reporter gene and bait protein; each member of the library directs the synthesis of a candidate interacting protein fused to an invariant gene activation domain tag. Those library-encoded proteins that physically interact with the promoter-bound bait protein are referred to as "prey" proteins. Such bound prey proteins (via their activation domain tag) detectably activate the transcription of the downstream reporter gene and provide a ready assay for identifying particular cells which harbor a DNA clone encoding an interacting protein of interest. Preferably, in this system, the bait protein (i.e., the protein containing a site-specific DNA binding domain) is transcriptionally inert, and the reporter genes (which are bound by the bait protein) have essentially no basal transcription.

Each component of the system is now described in more detail.

Bait Proteins

In one preferred selection host strain, the DNA binding moiety of the bait protein is derived from the bacterial LexA protein. The use of a LexA DNA binding domain provides certain advantages. For example, in yeast, the LexA moiety contains no activation function and has no known effect on transcription of yeast genes (Brent and Ptashne, Nature 312:612–615, 1984; Brent and Ptashne, Cell 43:729–736, 1985). In addition, use of the LexA rather than the GAL4 DNA-binding domain allows conditional expression of prey proteins in response to galactose induction; this facilitates detection of prey proteins which might be toxic to the host cell if expressed continuously. Finally, the use of LexA allows knowledge regarding the interaction between LexA and the LexA binding site (i.e., the LexA operator) to be exploited for the purpose of optimizing operator occupancy.

The bait protein illustrated in FIG. 2A also includes a LexA dimerization domain; this optional domain facilitates efficient LexA dimer formation. Because LexA binds its DNA binding site as a dimer, inclusion of this domain in the bait protein also optimizes the efficiency of operator occupancy and/or the geometry of the bound bait protein to effect transcription (Golemis and Brent, Mol. Cell Biol. 12:3006–3014, 1992).

LexA represents a preferred DNA binding domain in the invention. However, any other transcriptionally-inert or essentially transcriptionally-inert DNA binding domain may be used in the interaction trap system; such DNA binding domains are well known and include the DNA binding portions of the proteins ACE1 (CUP1), lambda cI, lac repressor, jun fos, or GCN4. For the above-described reasons, the GAL4 DNA binding domain represents a slightly less preferred DNA binding moiety for the bait proteins.

Bait proteins may be chosen from any protein of known or suspected diagnostic or therapeutic importance. Preferred bait proteins include oncoproteins (such as myc, particularly the C-terminus of myc, ras, src, fos, and particularly the oligomeric interaction domains of fos) or any other proteins involved in cell cycle regulation (such as kinases, phosphatases, the cytoplasmic portions of membrane-associated receptors). In each case, the protein of diagnostic or therapeutic importance would be fused to a known DNA binding domain as generally described herein.

Reporters

One preferred host strain according to the invention contains two different reporter genes, the LEU2 gene and the lacZ gene, each carrying an upstream binding site for the bait protein. Such reporter genes include, as an upstream binding site, one or more LexA operators in place of their native Upstream Activation Sequences (UASs). These reporter genes may be integrated into the chromosome or may be carried on autonomously replicating plasmids (e.g., yeast 2µ plasmids).

A combination of two such reporters is preferred in the invention for a number of reasons. First, the LexAop-LEU2 construction allows cells that contain interacting proteins to select themselves by growth on medium that lacks leucine, facilitating the examination of large numbers of potential interactor protein-containing cells. Second, the LexAop-lacZ reporter allows LEU$^+$cells to be quickly screened to confirm an interaction. And, third, among other technical considerations (see below), the LexAop-LEU2 reporter provides an extremely sensitive first selection, while the LexAop-lacZ reporter allows discrimination between proteins of different interaction affinities.

Although the reporter genes described herein represent a preferred embodiment of the invention, other equivalent genes whose expression may be detected or assayed by standard techniques may also be employed in conjunction with, or instead of, the LEU2 and lacZ genes. Examples of other useful genes whose transcription can be detected include amino acid and nucleic acid biosynthetic genes (such as yeast HIS3, URA3, TRP1, and LYS2) GAL1, E. coli galK (which complements the yeast GALL gene), and the higher cell reporter genes CAT, GUS, and any gene encoding a cell surface antigen for which antibodies are available (e.g., CD4). In short, reporter genes may encode any enzyme that provides a phenotypic marker, for example, a protein that is necessary for cell growth or a toxic protein leading to cell death, or one encoding a protein detectable by color assay or one whose expression leads to an absence of color. Particularly preferred reporter genes are those encoding fluorescent markers, such as the GFP gene (i.e., Green Fluorescent Protein gene). Reporter genes may facilitate either a selection or a screen for reporter gene expression, and quantitative differences in reporter gene expression may be measured as an indication of interaction affinities.

Prey Proteins

In the selection described herein, a fourth DNA construction was utilized which encoded a series of candidate interacting proteins, each fused to an activation domain (i.e., prey proteins). A preferred prey protein includes an invariant N-terminal moiety. This moiety carries, amino to carboxy terminal, an ATG for protein expression, an optional nuclear localization sequence, a weak activation domain (e.g., the B112 or B42 activation domains of Ma and Ptashne, Cell 51:113, 1987), and an optional epitope tag for rapid immunological detection of fusion protein synthesis.

Prey proteins other than those described herein are also useful in the invention. For example, cDNAs may be constructed from any mRNA population and inserted into an equivalent expression vector. Such a library of choice may be constructed de novo using commercially available kits (e.g., from Stratagene, La Jolla, Calif.) or using well established preparative procedures (see, e.g., *Current Protocols in Molecular Biology*, New York, John Wiley & Sons, 1987). Alternatively, a number of cDNA libraries (from a number of different organisms) are publically and commercially available; sources of libraries include, e.g., Clontech (Palo Alto, Calif.) and Stratagene (La Jolla, Calif.). It is also noted that prey proteins need not be naturally occurring full length polypeptides. For example, a prey protein may be encoded by a synthetic sequence or may be the product of a randomly generated open reading frame or a portion thereof. In one particular example, the prey protein includes only an interaction domain; such a domain may be useful as a therapeutic to modulate bait protein activity.

Similarly, other activation domains may be substituted for the B112 or B42 portions of the prey molecule; such activation domains are preferably weak activation domains, i.e., weaker than the GAL4 activation region II moiety and preferably no stronger than B112 (as measured, e.g., by a comparison with GAL4 activation region II or B112 in parallel β-galactosidase assays using lacZ reporter genes);

such a domain may, however, be weaker than B112. In particular, the extraordinary sensitivity of the LEU2 selection scheme (described above) allows even extremely weak activation domains to be utilized in the invention. Examples of other useful weak activation domains include B17 and the amphipathic helix (AH) domains described in Ma and Ptashne (Cell 51:113, 1987), Ruden et al. (Nature 350:426–430, 1991), and Giniger and Ptashne (Nature 330:670, 1987).

Finally, the prey proteins, if desired, may include other optional nuclear localization sequences (e.g., those derived from the GAL4 or MATα2 genes) or other optional epitope tags (e.g., portions of the c-myc protein or the flag epitope available from Immunex). These sequences optimize the efficiency of the system, but are not absolutely required for its operation. In particular, the nuclear localization sequence optimizes the efficiency with which prey molecules reach the nuclear-localized reporter gene construct(s), thus increasing their effective concentration and allowing one to detect weaker protein interactions; and the epitope tag merely facilitates a simple immunoassay for fusion protein expression.

Those skilled in the art will also recognize that the above-described reporter gene, DNA binding domain, and gene activation domain components may be derived from any appropriate eukaryotic or prokaryotic source, including yeast, mammalian cell, and prokaryotic cell genomes or cDNAs as well as artificial sequences. Moreover, although yeast represents a preferred host organism for the interaction trap system (for reasons of ease of propagation, genetic manipulation, and large scale screening), other host organisms such as mammalian cells may also be utilized. If a mammalian system is chosen, a preferred reporter gene is the sensitive and easily assayed CAT gene; useful DNA binding domains and gene activation domains may be chosen from those described above (e.g., the LexA DNA binding domain and the B42 or B112 activation domains).

Interaction Trap System for Identifying Multi-Protein Interactions

One example of an interaction trap system according to the invention is now described. This interaction trap detects multi-protein interactions, and identifies and isolates proteins participating in such interactions. The particular system now described is exemplary and makes use of a large panel of bait-containing yeast strains. In general, according to this method, a yeast strain harboring an uncharacterized prey protein is mated with each of the members of a bait strain panel, and interactions are detected by screening. This method is shown schematically in FIG. 1. Using an interaction trap system, a set of seven proteins from embryonic *Drosophila melanogaster* were initially isolated which interacted with two Drosophila cyclin-dependent kinases, DmCdc2 and DmCdc2c. These proteins, termed Cyclin Dependent Kinase Interactors ("Cdis") were then characterized using an interaction-mating technique according to the invention.

The interaction-mating technique relies on the fact that haploid yeast have two different mating types which mate by fusing to form diploids (Herskowitz, Microbiol. Rev. 52:536, 1988). In an interaction mating, the bait and activation-tagged proteins are each expressed in different haploid strains and are brought together by mating the two strains. By this means, large numbers of individual protein-protein interactions can be tested, and the results of these tests displayed as two dimensional arrays ("interaction matrices".

To characterize the Cdis, a collection of strains was constructed, each of which expressed a different bait. These strains were mated with test strains that contained different activation-tagged Cdis. Examination of the interaction matrices showed that each Cdi associated specifically with a distinct spectrum of cyclin dependent kinases, and that two different pairs of Cdis likely formed trimeric complexes with a Drosophila Cdk. These results suggest that interaction-mating is generally useful for detecting other multiprotein complexes, and for establishing binary connections between their components. In addition, the results suggest that interaction-mating may help assign functions to uncharacterized proteins, to dissect regulatory protein networks, and to identify domains involved in specific protein-protein interactions. This technique may thus aid in the analysis of protein sequences generated by genome sequencing efforts.

The Interaction-Mating System

In an example of one embodiment of the invention, a yeast interaction-mating system was designed as follows. The bait strains were haploid RFY206 derivatives (MATa; see below) that each contained a LexAop-lacZ reporter plasmid (pSH18–34; see below) and one of a panel of different bait plasmids. The prey strains were haploid EGY48 derivatives (MATα) that contained plasmids expressing different activation-tagged proteins (i.e., different pJG4–5 derivatives; see below) and that also contained a LexAop-LEU2 reporter gene sensitive enough to register transcription activation in diploids (in which LexAop reporters have been demonstrated to be less active). In these experiments, RFY206 derivatives were streaked in horizontal rows on a Glu ura⁻his⁻plate and grown for 3 days at 30° C. The EGY48 derivatives were streaked in vertical columns on a Glu trp⁻plate and grown for 2 days at 30° C. These two sets of streaks were then sequentially pressed onto the same replica velvet and lifted onto a YPD plate. The YPD master plates were incubated for 12–20 hours at 30° C., allowing the strains to mate and form diploids at the intersections of the horizontal and vertical streaks. The YPD master plates were then replica plated to the following indicator plates: (1) Glu ura⁻his⁻trp⁻ X-Gal ("Glu X-Gal"); (2) Gal ura⁻his⁻trp⁻ X-Gal ("Gal X-Gal"); (3) Glu ura⁻his⁻trp⁻leu⁻ ("Glu leu⁻"); and (4) Gal ura⁻his⁻trp⁻leu³¹ ("Gal leu⁻"). Typically, in any given experiment, two YPD master plates from two separate matings were tested on indicator replica plates.

Diploids were selected by using plates lacking nutrients required for growth of the parental haploid strains. On the Gal plates, synthesis of the activation-tagged proteins was induced. On the Leu⁻ plates, diploids grew only if they either contained an activation-tagged protein that interacted with the bait (growth on Gal leu⁻ only) or if the bait activated transcription (growth on Glu leu⁻ and Gal leu⁻). On the X-Gal plates, diploids turned blue either if there was a strong protein interaction (blue on Gal leu⁻ only) or if the bait itself was a strong transcription activator (blue on Glu leu⁻ and Gal leu⁻). We therefore scored interactions by the presence of Galactose-dependent Leu⁺ diploids. Because the lacZ reporter was not as sensitive as the LEU2 reporter, some weak interactions resulted in diploids that were white on Gal X-Gal. We also employed a variant of this procedure in which one plate contained a lawn of a single EGY48 derivative that expressed an activation-tagged protein, and a second plate contained a grid of different bait strains, which we replica plated onto YPD and then onto indicator plates as described above.

Interactions Between Cdis and Cdc2 Kinases (Cdks)

We used interaction-mating to characterize a set of seven Drosophila Cdk interactors (Cdis) identified in interactor hunts with either of two Drosophila Cdks, Dmcdc2 and Dmcdc2c (Lehner et al., EMBO J. 9:3573, 1990) as baits. These proteins are shown below in Table 1.

TABLE 1

Cyclin Dependent Kinase Interactors.*

| Cdi | Function[a] | Isolated With |
|---|---|---|
| Cdi2 | Cks1 | Dmcdc2 |
| Cdi3 | D-type cyclin | Dmcdc2, Dmcdc2c |
| Cdi4 | unknown | Dmcdc2c |
| Cdi5 | novel cyclin | Dmcdc2c |
| Cdi7 | E-type cyclin[†] | Dmcdc2 |
| Cdi11 | unknown | Dmcdc2c |
| Cdi12 | unknown | Dmcdc2c |

*Cdis were isolated from a Drosophila embryonic cDNA library in interactor hunts using the indicated Drosophila Cdk.
[a]From sequence information.
[†]Drosophila cyclin E was also isolated by Richardson et al. (Richardson et al., Development 119:673, 1993).

In these experiments, we mated haploid bait strains expressing either no LexA or one of a number of LexA fusions to either Drosophila, human, or yeast Cdc2-type kinases with haploid strains that contained different activation-tagged Cdis. Indicator plates (as described above) were incubated at 30° C. for 2 days. Galactose-dependent growth of the diploids in the absence of leucine indicated an interaction between the bait and activation-tagged protein that activated the LEU2 reporter. The strength of an interaction was estimated by the amount of lacZ expression, monitored as blue color on X-Gal plates.

In particular, interactions were tested between the Drosophila Cdis (Cdi2, Cdi3, Cdi4, Cdi5, Cdi7, Cdi11, and Cdi12) and the following Drosophila, human, and yeast Cdks: DmCdc2, DmCdc2c, HsCdc2, HsCdk2, HsCdk3, HsCdk4, and ScCdc28. The results are shown in Tables 2 and 3.

TABLE 2

| | Glu | | | | Gal | | | | |
|---|---|---|---|---|---|---|---|---|---|
| | Vector | Cdi2 | Cdi3 | Cdi4 | Vector | Cdi2 | Cdi3 | Cdi4 | |
| DmCdc2 | − | − | − | − | − | + | + | +/− | Leu⁻ |
| DmCdc2c | − | − | − | − | − | + | + | + | |
| HsCdc2 | − | − | − | − | − | + | − | − | |
| HsCdk2 | − | − | − | − | − | + | − | − | |
| HsCdk3 | − | − | − | − | − | + | + | + | |
| HsCdk4 | − | − | − | − | − | − | + | − | |
| ScCdc28 | − | − | − | − | − | + | + | − | |
| Vector | − | − | − | − | | | | | |
| DmCdc2 | W | W | W | W | W | B | B | W | X-Gal |
| DmCdc2c | W | W | W | W | W | B | B | B | |
| HsCdc2 | W | W | W | W | W | B | W | W | |
| HsCdk2 | W | W | W | W | W | W | W | W | |
| HsCdk3 | W | B | W | W | W | B | W | W | |
| HsCdk4 | W | W | W | W | W | W | B | W | |
| ScCdc28 | W | W | W | W | W | B | W | W | |
| Vector | W | W | W | W | | | | | |

− = NO GROWTH
+ = GROWTH
W = WHITE
B = BLUE

TABLE 3

| | Glu | | | | Gal | | | | |
|---|---|---|---|---|---|---|---|---|---|
| | Cdi5 | Cdi7 | Cdi11 | Cdi12 | Cdi5 | Cdi7 | Cdi11 | Cdi12 | |
| DmCdc2 | − | − | − | − | − | + | − | − | Leu⁻ |
| DmCdc2c | − | − | − | − | + | − | + | + | |
| HsCdc2 | − | − | − | − | − | − | − | − | |
| HsCdk2 | − | − | − | − | − | − | − | − | |
| HsCdk3 | − | − | − | − | − | − | − | + | |
| HsCdk4 | − | − | − | − | − | − | − | + | |
| ScCdc28 | − | − | − | − | + | − | − | + | |
| Vector | − | − | − | − | − | − | − | − | |
| DmCdc2 | W | W | W | W | W | W | W | W | X-Gal |
| DmCdc2 | W | W | W | W | W | W | W | W | |
| HsCdc2 | W | W | W | W | W | W | W | W | |
| HsCdk2 | W | W | W | W | W | W | W | W | |
| HsCdk3 | W | W | W | W | W | W | W | W | |
| HsCdk4 | W | W | W | W | W | W | W | W | |
| ScCdc28 | W | W | W | W | B | W | W | W | |
| Vector | W | W | W | W | W | W | W | W | |

As indicated by Galactose-dependent growth of diploids on leu⁻ medium, the Cdis interacted with distinct spectra of Cdks. For example, Cdi2 interacted with all Cdks tested except human Cdk4, whereas the other Cdis interacted with only one or a smaller number of them. Differences in the amount of Galactose-dependent lacZ expression suggested that some interactions were stronger than others. For example, Cdi2 interacted most strongly with Cdk3; this interaction was so strong that even the basal expression of the Cdi2 protein on Glucose medium was sufficient to activate both reporters, thus allowing some growth on Glu leu⁻ and producing some blue color on Glu X-Gal. Cdi3 interacted most strongly with Cdk4. These results show that the cyclins (Cdi3, Cdi5, and Cdi7) have marked preferences for particular Cdk partners. In the most dramatic example, the novel cyclin, Cdi5, interacted with Dmcdc2c but did not interact detectably with Dmcdc2, while the E-type cyclin, Cdi7, showed an opposite preference. By contrast, the D-type cyclin, Cdi3, interacted about equally with Dmcdc2 and Dmcdc2c, but interacted most strongly with human Cdk4, suggesting that a relevant partner of Cdi3 in Drosophila may be a Cdk4 homolog.

Interactions Between Cdis

We used a similar interaction-mating assay to examine interactions between the Cdis (Cdi2, Cdi3, and Cdi4) and a large number of baits (Drosophila Cdi2, Cdi3, Cdi4, Cdi11, a Bicoid derivative, Raf, and Human Max). These results are shown in Table 4.

on the cyclin-kinase pair it interacts with (Cdi3-Dmcdc2c) that is different than the function Cdi2 confers on the cyclin-kinase pair it recognizes (Cdi5-Dmcdc2c).

In sum, inspection of the interaction matrices showed that the Cdis did not interact with a large set of unrelated proteins, but showed distinct spectra of interaction with different Cdks and other Cdis. Further examination of this data showed several results. First, Cdi2, a Cks homolog, interacted with all Cdks tested, except for human Cdk4, suggesting that it interacts with conserved structural elements of these related proteins. Second, Cdi5, a novel cyclin, interacted with Dmcdc2c and not Dmcdc2, while Cdi7, an E-type cyclin, interacted with Dmcdc2 but not Dmcdc2c, suggesting that such differences in interaction affinity may help explain the observed preference of cyclins for different Cdk partners. Third, Cdi3, a D-type cyclin, interacted with both Drosophila Cdks, S. cerevisiae Cdc28, and human Cdk3, and most strongly with human Cdk4. This suggests that, as in human cells where cyclin D forms active complexes with Cdk4, a relevant partner of cyclin D in Drosophila may be a hitherto unidentified Cdk4 homolog. Finally, Cdi2 (Cks homolog), interacted with Cdi5 (novel cyclin), and Cdi11 (novel protein) interacted with Cdi3 (D-type cyclin) and with Cdi4 (a second novel protein), suggesting that these proteins may function in two different multiprotein complexes, one of which contains Dmcdc2c, Cdi2, and Cdi5, the other Dmcdc2c, Cdi3, and Cdi11.

Our results suggest a number of uses for the interaction-mating technique. Some of these are consequences of the

TABLE 4

| | Glu | | | | Gal | | | | |
|---|---|---|---|---|---|---|---|---|---|
| | Vector | Cdi2 | Cdi3 | Cdi4 | Vector | Cdi2 | Cdi3 | Cdi4 | |
| Cdi2 | + | + | + | + | + | + | + | + | Leu⁻ |
| Cdi3 | − | − | − | − | − | − | − | − | |
| Cdi5 | − | − | − | − | − | + | − | − | |
| Cdi11 | − | − | − | − | − | − | + | + | |
| HsMax | − | − | − | − | − | − | − | − | |
| DmRaf | − | − | − | − | − | − | − | − | |
| DmBicoid | − | − | − | − | − | − | − | − | |
| Cdi2 | W | W | W | W | W | W | W | W | X-Gal |
| Cdi3 | W | W | W | W | W | W | W | W | |
| Cdi5 | W | W | W | W | W | W | W | W | |
| Cdi11 | W | W | W | W | W | W | W | W | |
| HsMax | W | W | W | W | W | W | W | W | |
| DmRaf | W | W | W | W | W | W | W | W | |
| DmBicoid | W | W | W | W | W | W | W | W | |

Results from matings (performed as described above) indicated that the Cdis did not interact with Drosophila Raf kinase, human Max, or 30 other tested baits, extending previous findings in haploids indicating that the observed interactions of the Cdis are specific. More importantly, this interaction-mating approach indicated that Cdis interacted with other Cdis: the Cdi5 bait interacted with activation-tagged Cdi2, and the Cdi11 bait interacted with activation-tagged Cdi3 and Cdi4. This result is consistent with the idea that the two sets of proteins may form ternary complexes. Ternary complexes are expected for Cdi2 and Cdi5, whose sequences respectively identify them as Cks1 and cyclin homologs (Table 1), proteins known to simultaneously bind Cdks. Cdi11, on the other hand, has no similarity to previously identified proteins, but the fact that it interacts with two different cell cycle regulators, a cyclin and a kinase, and not with other proteins, supports the idea that it functions in cell cycle regulation. Moreover, the fact that Cdi11 is of a novel sequence class suggests that it may confer a function fact that, by obviating the need to introduce DNA encoding potentially interacting proteins into bait strains by transformation, interaction-mating greatly simplifies established interaction trap experiments. Multiple hunts can now be conducted by collecting a very large number of cells transformed with interaction library members, freezing the collection, and mating thawed aliquots with individual bait strains. In addition, it facilitates a determination that candidate interactors are specific by allowing one to perform quick tests of interaction with a number of different baits.

Similarly, analysis of interaction matrices extends one form of classical suppressor genetics. Consider the fact that two similar proteins, the cyclins Cdi5 and Cdi7, show contrasting interaction specificity for two other proteins of similar sequence, DmCdc2 and DmCdc2c. This finding is formally similar to the extreme allele specificity sometimes found for second site supressors in classical genetics (for example, between the cheC and cheZ gene products), which is a strong genetic indication of direct protein-protein interaction. Observation of strong and reciprocal interaction specificity between sets of proteins of related sequence in interaction mating experiments likely constitutes equivalent genetic evidence for direct protein protein interaction. Moreover, we note that such findings open the way to construction of appropriate "amino acid swap" mutations to change specificity and further delineate the residues involved in the contact.

Finally, by greatly increasing the number of individual interactions that can be tested, interaction mating can reveal binary protein-protein interactions that may signal multiprotein complexes. It was found, for example, that two Drosophila Cdk interacting proteins, Cdi2 and Cdi5, interacted with each other. This indicates that Cdi2, Cdi5, and the kinase, Dmcdc2c, each have a surface for interaction with the other two proteins or for interaction with a common yeast protein acting as a bridging molecule (e.g., Cdc28). This suggests that these proteins may form a trimeric complex. We obtained similar result with Dmcdc2c, Cdi3, and Cdi11. Such analysis is generally useful for establishing connectivity between proteins in known multiprotein complexes and in sets of proteins known to interact genetically.

Interaction-mating also facilitates identification of previously unsuspected interactions of potential biological significance. For example, the Drosophila D-type cyclin, Cdi3, interacts with another protein, Cdi11, which interacts specifically with Drosophila Cdks but whose sequence so far does not allow prediction of its function. Cdi11 may thus exemplify a new type of protein that modulates activity of cyclin/Cdk complexes. The cumulative probability that a biologically relevant but previously unsuspected interaction will be revealed by this approach increases with the number of potential interactions tested. Identification of unsuspected interactions is generally useful in suggesting protein function, and helps position proteins within genetic and biochemical pathways. The ability to estimate relative interaction affinities using the lacZ reporters adds an additional dimension to the interaction matrices and may aid such analysis. Such analyses may also help identify new loci affected in genetic diseases for which allelic variants of one gene are already implicated. Affected individuals who lack lesions in the first gene may have mutations in other genes involved in the process; one criterion for identification of such genes is to identify those encoding proteins whose interaction with the first protein is affected by mutations in the first protein associated with the disease state.

Even absent a biological connection between interacting proteins, structural information about the contact may be derived from consideration of the protein sequences. If, for example, Cdi3 had been isolated by some other method and tested for interaction with the sixty bait strains used herein, we would have learned that Cdi3 frequently makes contacts with serine/threonine kinases, suggesting that Cdi3 contacts common sequence or structural elements in these proteins. The larger the panel of baits, the more it constitutes a representative protein surface space that can be searched for such interaction motifs. As above, the addition of a third dimension, that reflects affinity, to the interaction matrices, may aid structural analysis by this technique and may facilitate the design of agonist or antagonist molecules which increase or decrease (respectively) the interactions between such molecules.

Since there are hundreds of strains that contain different bait proteins, and since their number is increasing, the power of interaction-mating to reveal connections between proteins is expanding. This technique augments established genetic methods, such as epistasis and suppressor analysis, that suggest protein function. Display of this information in interaction matrices and its analysis by computational techniques should allow analysis of the topology of the underlying protein network, which may aid the assignment of protein function and the identification of genetic pathways. Analysis of interaction matrices also aids efforts, such as genome characterization, in which tentative hypotheses about newly identified genes are useful.

Panels of Test Proteins

The interaction-mating technique is facilitated by the availability of a large panel of test proteins against which candidate interacting proteins are tested. One such panel according to the invention is encoded by a series of fusion genes, each member of the series encoding a protein categorized according to function and fused to a DNA binding domain. For example, applicants have available to them the following test protein panels: (1) Signal Transduction (including p53 and fragments thereof, Fus3, lck, the cytoplasmic domain of CD45, the cytoplasmic domain of LAR, thyroid receptor, exon 16 of the human insulin receptor, the $\beta$ domain of the insulin receptor, amino acids 1–93 of c-jun, the Drosophila abl SH3 domain, the Drosophila ERK, E2-2, tailess, disheveled, raf kinase, deltex, cdc2, cdc2c, cyclin C, Cdi2, Cdi3 D-like cyclin, Cdi5, Cdi11, and Cdi12 proteins, Drosophila notch amino acids 1827–2258, GAP43, CDK4, the human Cdc2, Cdc2 G154N, Cdc2 E57Q, Cdc2 E57N, Cdi1, Cdk2, Cdk3, cyclin C, cyclin D, cyclin E, and Rb proteins, and Saccharomyces cerevisiae Cdc28 protein), (2) DNA Replication (including the SV40 large T and Drosophila PCNA proteins), (3) Nuclear transactions other than DNA replication (including Sp1 region B, zebrafish goosecoid, SPT5 amino acids 12–1063, Pbx1, E2-5, E2-2, REPR RNA editing protein, the Drosophila m(beta), groucho, FTZ-F1, ftz HD, Enhancer of split, sisb-AC, sisb-32, tra2, daughterless, bicoid, bicoid polyQ, and hairy proteins, the Drosophila bicoid prd repeat 2–95 and bicoid hd amino acids 50–160, HPV-16 E6 and E7, Mxi1, max, the c-terminus of c-myc, chicken HOX4.6(D11), paired, id, yeast Ssn6, Su2(2), Bim1, Psc, Pcc, human Rb, Max HLH zip, and c-Myc HLH zip proteins), and (4) Intermediary Metabolism (including the YRC67p, Sec12, rat (Na,K) ATPase α2, and peroxisome target signal proteins). Cytokines represent another source of bait proteins. Each of the above proteins is publically available. Each of these proteins is expressed in a haploid yeast equipped with the appropriate genetic markers to facilitate yeast mating with haploid strains that express candidate prey proteins. Preferably, the members of the test panel also include a reporter gene that is distinct from the reporter gene carried by the prey protein haploids. In this way, interactions can be detected and confirmed and the strength of the interaction can be simultaneously assayed (e.g., by the use of a LEU2 and lacZ reporter gene pair).

Yeast Manipulations

Standard microbiological techniques and media (Ausubel et al., *Current Protocols in Molecular Biology*, supra); Guthrie and Fink, *Guide to Yeast Genetics and Molecular Biology*, vol. 194, 1991) were used for all yeast manipulations. Media designations are as follows: YPD is YP (yeast extract plus peptone) medium with 2% Glucose. Minimal drop-out media (Ausubel et al., supra) are designated by the component that is left out, i.e., ura⁻ medium lacks uracil, leu⁻ medium lacks leucine, his⁻ medium lacks histidine, and trp⁻ medium lacks tryptophan. In some cases, two or more components are missing, for example, ura⁻ his⁻. Each minimal drop-out medium contains either 2% Glucose (Glu) or 2% Galactose plus 1% raffinose (Gal); raffinose aids growth and does not induce or repress the GAL1 promoter. X-Gal plates were similar to minimal drop out plates but contained X-Gal (5-bromo-4-chloro-indolyl-β-D-Galactopyranoside) and a phosphate buffer at pH 7.0 (Ausubel et al., supra). DNA was introduced into yeast as in the protocol of Gietz et al. (Nuc. Acids. Res. 20:1425, 1992); transformants were selected and maintained on appropriate minimal drop-out plates.

Yeast Strains and Plasmids

RFY206 (Mata his3Δ200 leu2-3 lys2Δ201 ura3-52 trp1Δ::hisG) was made from yeast strain L4035 (a derivative of S288C). A deletion in the L4035 TRP1 gene was made using pNKY1009 as described (Alani et al., Genetics 116:541 1987) to yield RFY205 (Matα his3Δ200 leu2-3 lys2Δ201 ura3-52 trp1Δ::hisG). The mating type of RFY205 was switched as described (Jensen and Herskowitz, Cold Spring Harbor Symp. Quant. Biol. 49:91, 1984) with pJH132 (White and Haber, EMBO J. 9:663, 1990), which contains the HO gene under the control of the GAL10 promoter to yield RFY206. EGY48 (Matα his3 leu2::3Lexop-LEU2 ura3 trp1 LYS2; Gyuris et al., supra), contains a chromosomal LEU2 gene (3Lexop-LEU2) with its upstream regulatory elements replaced with three double overlapping, high affinity, LexA operators from the bacterial colE1 gene (Ebina et al., J. Biol. Chem. 258:13258, 1983).

pSH18-34, the lacZ reporter plasmid, is a pLR1Δ1 derivative (West et al., Mol. Cell Biol. 4:2467, 1984) similar to lacZ reporters previously described (Brent and Ptashne, Cell 43:729, 1985; Golemis and Brent, Mol. Cell Biol. 12:3006, 1992; Hanes and Brent, Cell 57:1275, 1989); it contains the yeast 2μ replication origin, the URA3 gene, and a GAL1-lacZ fusion with the GAL1 upstream regulatory elements replaced with 4 colE1 LexA operators. Activation-tagged proteins were conditionally expressed from the GAL1 promoter on plasmid pJG4-5 (Gyuris et al., supra) which contains the yeast 2μ origin and TRP1 gene. pRF4-5-Cdi2, -Cdi3, -Cdi4, -Cdi5, -Cdi7, -Cdi11, and -Cdi12 are pJG4-5 derivatives that express Drosophila cDNAs isolated in Drosophila Cdk interactor hunts. As summarized in Table 1, some Cdis show sequence similarity to previously identified proteins such as Cks and cyclins, while others, such as Cdi11 do not. LexA fusion (baits) were expressed from the ADH1 promoter on one of the bait expression vectors, pLexA (1–202)+PL (Ruden et al., Nature 350:250, 1991) or pEG202 (Gyuris et al., supra); both contain the yeast 2μ origin and HIS3 gene. Bait plasmids expressing LexA fused to human Cdc2, Cdk2, Cdk3, Cdk4, S. cerevisiae Cdc28, and Drosophila Cdc2 and Cdc2c have been described (Gyuris et al. supra). Cdi2, Cdi3, Cdi5, and Cdi11 bait expression plasmids were made by inserting EcoRI-XhoI fragments from the respective pRF4-5-Cdi plasmids into the backbone of pLexA(1–202)+PL cut with EcoRI and SalI. A "no LexA" control vector, pRFHMO, was made by deleting the SphI-SphI fragment that contained part of the ADH1 promoter and terminator and all of the LexA coding region from pLexA(1-202)+PL. The Drosophila Raf protein kinase bait was expressed from a pEG202-derivative provided by J. Duffy and N. Perrimon.

Interaction Trap

In a typical interaction trap, a yeast strain carries four components: a constitutively expressed LexA fusion (the "bait", a sensitive chromosomal LEU2 reporter with upstream LexA operators, a lacZ reporter plasmid chosen from a set with different numbers and types of LexA operators (Brent and Ptashne, supra), and a plasmid that directs, conditionally under the control of the GAL1 promoter, a protein which carries a nuclear localization sequence, the B42 transcription activation domain, and an epitope tag (Gyuris et al., supra). Activation-tagged proteins are expressed on Gal medium but not on Glu. Cells that contain proteins that interact with the bait form colonies on Gal leu⁻ plates but not Glu leu⁻ plates. Most lacZ reporters used are less sensitive than the LEU2 reporter so that, on Gal X-Gal plates, yeast containing strong interactors form blue colonies, but yeast containing weak interactors form light blue or white colonies.

Other Embodiments

As described herein, the invention features a method for detecting and analyzing protein-protein interactions. Typically, in the above experiments, the bait protein is fused to the DNA binding domain, and the prey protein is fused to the gene activation domain. The invention, however, is readily adapted to other formats. For example, the invention also includes a "reverse" interaction trap in which the bait protein is fused to a gene activation domain, and the prey protein is fused to the DNA binding domain. Again, an interaction between the bait and prey proteins will result in activation of reporter gene expression. Such a reverse interaction trap system, however, depends upon the use of prey proteins which do not themselves activate reporter gene expression.

Kits including the components of any of the interaction trap systems described herein are also included in the invention.

Other embodiments are within the following claims.

What is claimed is:

1. A set of DNA molecules, each molecule encoding a different natural occuring candidate interacting protein fused to a DNA binding domain to which it is not naturally bonded, wherein the set comprises at least ten different DNA molecules and wherein the amino acid sequence of said candidate interacting protein is known.

2. A set of DNA molecules, each molecule encoding a different naturally occurring candidate interacting protein fused to a weak gene activating domain to which it is not naturally bonded, wherein the set comprises at least ten different DNA molecules and wherein the amino acid sequence of said candidate interacting protein is known.

3. The set of DNA molecules of claims 1 or 2, wherein each of said candidate interacting proteins is involved in signal transduction.

4. A set of eukaryotic cells, each cell containing one of said set of DNA molecules of claims 1 or 2.

5. The set of eukaryotic cells of claim 4, wherein said cells are yeast cells.

* * * * *